United States Patent [19]

Heacock

[11] Patent Number: 5,784,148
[45] Date of Patent: Jul. 21, 1998

[54] WIDE FIELD OF VIEW SCANNING LASER OPHTHALMOSCOPE

[76] Inventor: Gregory Lee Heacock, 505 Timber Valley Rd., Atlanta, Ga. 30342

[21] Appl. No.: 629,584

[22] Filed: Apr. 9, 1996

[51] Int. Cl.$^6$ ............................... A61B 3/10; A61B 3/14
[52] U.S. Cl. ........................... 351/221; 351/206; 351/215
[58] Field of Search ................................ 351/205, 206, 351/207, 209, 210, 211, 212, 215, 221

[56] References Cited

U.S. PATENT DOCUMENTS

| | | | |
|---|---|---|---|
| 4,579,430 | 4/1986 | Bille | 351/206 |
| 4,781,453 | 11/1988 | Kobayashi | 351/206 |
| 5,090,798 | 2/1992 | Kohayakawa | 351/221 |
| 5,537,162 | 7/1996 | Hellmuth et al. | 351/206 |

*Primary Examiner*—Huy Mai
*Attorney, Agent, or Firm*—McAndrews, Held & Malloy, Ltd.

[57] ABSTRACT

A scanning laser ophthalmoscope with a wide field of view provides a color image of an interior portion of a patient's eye at varying depths while the patient is simultaneously presented with a fixation target designed to probe his visual function. The scanning laser ophthalmoscope includes an illumination system, a capturing and detection system and a target image generating system wherein the optical paths of each of these systems is separated by one or more beam splitters to prevent a chief ray from the patient's eye from being blocked so as to eliminate shading off effects in the captured image. A simplified scanning system is employed that includes only one scanner with a moveable reflective surface. A passive, stationary optical element is employed to generate a line of light from a point of light that impinges on the optical element, the line of light being scanned in a direction perpendicular to the line by the single scanner.

61 Claims, 8 Drawing Sheets

WIDE FIELD OF VIEW SCANNING LASER OPHTHALMOSCOPE

FIELD OF INVENTION

The present invention relates to a scanning laser ophthalmoscope with a wide field of view and more particularly to a scanning laser ophthalmoscope that allows the structure of a patient's eye at varying depths to be viewed while the patient is simultaneously presented with a fixation target designed to probe his visual function.

BACKGROUND OF THE INVENTION

Scanning laser ophthalmoscopes such as shown in U.S. Pat. Nos. 4,765,730 Webb; 4,764,006 Webb and 4,768,873 Webb are known to include a turning mirror to direct a laser beam to a multi-faceted rotating polygonal reflector scanner that scans a laser beam in a first direction to form a line of light. A second scanner is employed in the form of a galvanometer reflector scanner to scan the line of light generated by the first scanner in a second direction perpendicular to the first direction of scanning. The scanned light is directed to a patient's eye by a series of focusing mirrors. Light reflected from the patient's eye follows the same path via the scanners and focusing mirrors back to the turning mirror. The turning mirror is small so that the light reflected from the eye passes around it to an optical detector in the form of an avalanche diode. The output of the optical detector is coupled to the display to provide a two dimensional picture of the patient's retina. Although this type of scanning laser ophthalmoscope is capable of producing an image of the patient's retina without requiring the patient's pupil to be dilated with drugs and without requiring contact with the patient's eye, it has several drawbacks. First, the scanned laser light source employed in Webb's scanning laser ophthalmoscope is very bright and leaves the patient dazzled for some time following the diagnostic procedure implemented with the ophthalmoscope. Further, although the choice of apertures and their location as well as the placement of the second scanning mirror in the Webb system produces a device with few unwanted reflections, these system elements do not allow ocular tissues to be viewed at varying depths. The Webb system also suffers from complexity, high cost and provides a small field of view that is on the order of only 30°.

Another type of scanning laser ophthalmoscope is shown in U.S. Pat. No. 4,781,453 Kobayashi that utilizes a first acousto optical modulator for modulating the intensity of a laser beam to project a fixation target. The frequency of the drive signal for the first acousto optical modulator is also varied so as to select, with the use of a lens and device having a slit therein, a single wavelength of a laser beam having a number of wavelengths therein. The single selected wavelength of the laser is then passed to a scanning system. The scanning system includes a second acousto optical modulator that is driven so as to scan the selected wavelength of the laser in a first direction. Prior to scanning, however, the range of the second acousto optical modulator must be changed to accommodate the selected wavelength of the laser. The scanned laser is guided by relay lenses from the second acousto optical modulator to a mirror that is mounted on a galvanometer for scanning the laser in a second direction perpendicular to the scanning direction of the second acousto optical modulator. A small mirror then reflects the scanned light to a patient's eye. The light reflected from the eye passes around the small mirror and is captured by a lens and focused on a photosensor. A filter corresponding to the selected wavelength of the laser is disposed in front of the photosensor to allow passage of the selected light to the sensor. An image of the eye at a depth corresponding to the selected wavelength is stored in a frame memory associated with the selected wavelength, wherein the system includes different frame memories for the different wavelengths that can be selected. The different images stored in the frame memories can be selected via the electronics of the system for individual display in different colors. The Kobayashi ophthalmoscope is an extremely complex device in which the scanning range of the second acousto optical modulator must be changed to accommodate a selected wavelength of the laser light each time a new wavelength is selected via the first acousto optical modulator. Further, the filter disposed in front of the photo sensor must also be changed in accordance with the selected wavelength. The field of view of this scanning laser ophthalmoscope is also small, being on the same order as that described above for the Webb scanning laser ophthalmoscope.

Further, in both the Webb and Kobayashi systems, a mirror is disposed in the optical path of the light reflected from the patient's eye to the detector which causes a shading off effect. This shading off effect is realized as a darkening of the edges of an image feature with a gradual lightening of the image feature towards the center thereof. For example, this effect causes the displayed image of a blood vessel to appear as dark parallel lines with a lighter center therebetween. This effect is further exacerbated by the small aperture diameter employed in the image detection portion of the these systems. This small aperture although eliminating unwanted reflections from detection, brings substantially all of a given scene into focus at the same focal plane. The result is that the image of the patient's fundus appears similar regardless of the wavelength of the laser beam and the portion of the patient's eye at a particular depth therein reflecting the selected wavelength of the light.

SUMMARY OF THE INVENTION

In accordance with the present invention, the disadvantages of prior scanning laser ophthalmoscopes have been overcome. The scanning laser ophthalmoscope of the present invention provides a wide field of view and allows the structure of a patient's eye at varying depths therein to be viewed while the patient is simultaneously presented with a fixation target designed to probe his visual function. The scanning laser ophthalmoscope of the present invention is extremely simplified compared to prior devices and eliminates the shading off effects found in the displayed eye images produced by prior scanning laser ophthalmoscopes.

More particularly, the scanning laser ophthalmoscope of the present invention includes a source of laser light that is scanned by a scanning system for generating a two dimensional area of illumination. A first beam splitter reflects the illumination from the scanning system towards a patient's eye and also passes therethrough light reflected from the patient's eye. A second beam splitter that is coaxial with the first beam splitter receives light reflected from the patient's eye and passed through the first beam splitter. The second beam splitter reflects this received light to an image capturing system. The image capturing system detects the light reflected from the patient's eye and generates an image of an interior portion thereof from the detected light. A video display generates a moveable target image thereon wherein the video display is positioned with respect to the first and second beam splitters such that light from the video display passes through the beam splitters to the patient's eye. The target image thus generated is perceivable by the patient while the patient's fundus is simultaneously being illuminated and an image of an interior portion of the patient's eye is being captured.

In accordance with the present invention, shading off in the displayed image captured by the scanning laser ophthalmoscope is prevented because there is no scanner or mirror in the system that totally blocks light in a given region of the optical path from the patient's eye to the image capturing and detection system. This is unlike prior scanning laser ophthalmoscopes in which a scanner or mirror blocks the chief ray reflected at any given position in the patient's eye on its path to the image capturing and detection optics. Further, by separating the illumination system from the target video generation system, the problems of synchronizing the target video generation with the frequency of the scanning system is eliminated, greatly simplifying the electronics of the scanning laser ophthalmoscope of the present invention.

In accordance with another feature of the present invention, the scanning system includes only one scanner with a moveable reflective surface and a passive, stationary optical element. The passive optical element is positioned in a path of the laser light such that the light impinges on the optical element at a point and the optical element generates a line of light from that point. The single scanner with moveable reflective surface is then used to scan the line of light generated by the passive optical element in a direction perpendicular to the line so as to generate the two dimensional area of illumination. Because only a single scanner with a moveable reflective surface is employed as opposed to two such scanners, the scanning laser ophthalmoscope is more rugged and compact than prior devices. Further, because a passive, stationary optical element is employed as opposed to an active optical device, such as an acousto optical modulator that requires a drive signal to scan, the electronics of the present scanning laser ophthalmoscope are again greatly simplified.

In accordance with a further feature of the present invention, the source of laser light generates light having a number of wavelengths therein that are simultaneously scanned by the scanning system and directed to the patient's eye wherein different portions of the eye at different depths therein respond to different wavelengths of the laser light by reflecting a particular wavelength of light. A moveable field lens is provided to automatically capture an image of different parts of the eye at various depths therein in response to the mere movement of the field lens. A color eye image display is coupled to the image capturing and detection system so that as the captured image changes with the movement of the field lens the color of the eye image displayed automatically changes to depict the wavelength of light reflected by the eye portion focused on by the field lens.

In accordance with still another feature of the present invention, a nonsymmetric aspheric lens is employed to focus the target video from the target video generation system onto the patient's eye; to focus the illumination light from the illumination system on an area generally proximate to the patient's pupil; and to capture light reflected from the patient's eye and to focus that reflected light onto an image plane. This aspheric objective lens which is positioned between the patient's eye and the first beam splitter greatly simplifies the optical system of the scanning laser ophthalmoscope of the present invention and greatly reduces the optical components thereof.

Further, in accordance with another feature of the present invention, the laser light from the source is polarized in a first direction and a polarizer disposed between the image detector and the second beam splitter is polarized in a second direction that is different from the first direction to pass only desired light to the image detector. Thus, unwanted reflections are eliminated from the detected image.

A further feature of the present invention eliminates beating and blanking problems in the displayed image of the patient's eye. This problem is eliminated by scanning a line of light on the fundus of a patient's eye in an orientation relative to the eye that is perpendicular to the direction of the rastor lines of an image detector in the eye image capturing system. In particular, the scanned line of light is such that the line extends in a first direction relative to the eye and is scanned across the fundus in a direction perpendicular to the first direction of the line. The image detector of the image capturing system of the present invention includes a number of raster lines of image information wherein the raster lines, relative to the image of the interior portion of the patient's eye, extend in a second direction that is perpendicular to the first direction along which the scanned line extends.

These and other advantages and novel features of the present invention, as well as details of an illustrated embodiment thereof, will be more fully understood from the following description and drawings.

DESCRIPTION OF THE PREFERRED EMBODIMENT

Figure 1:
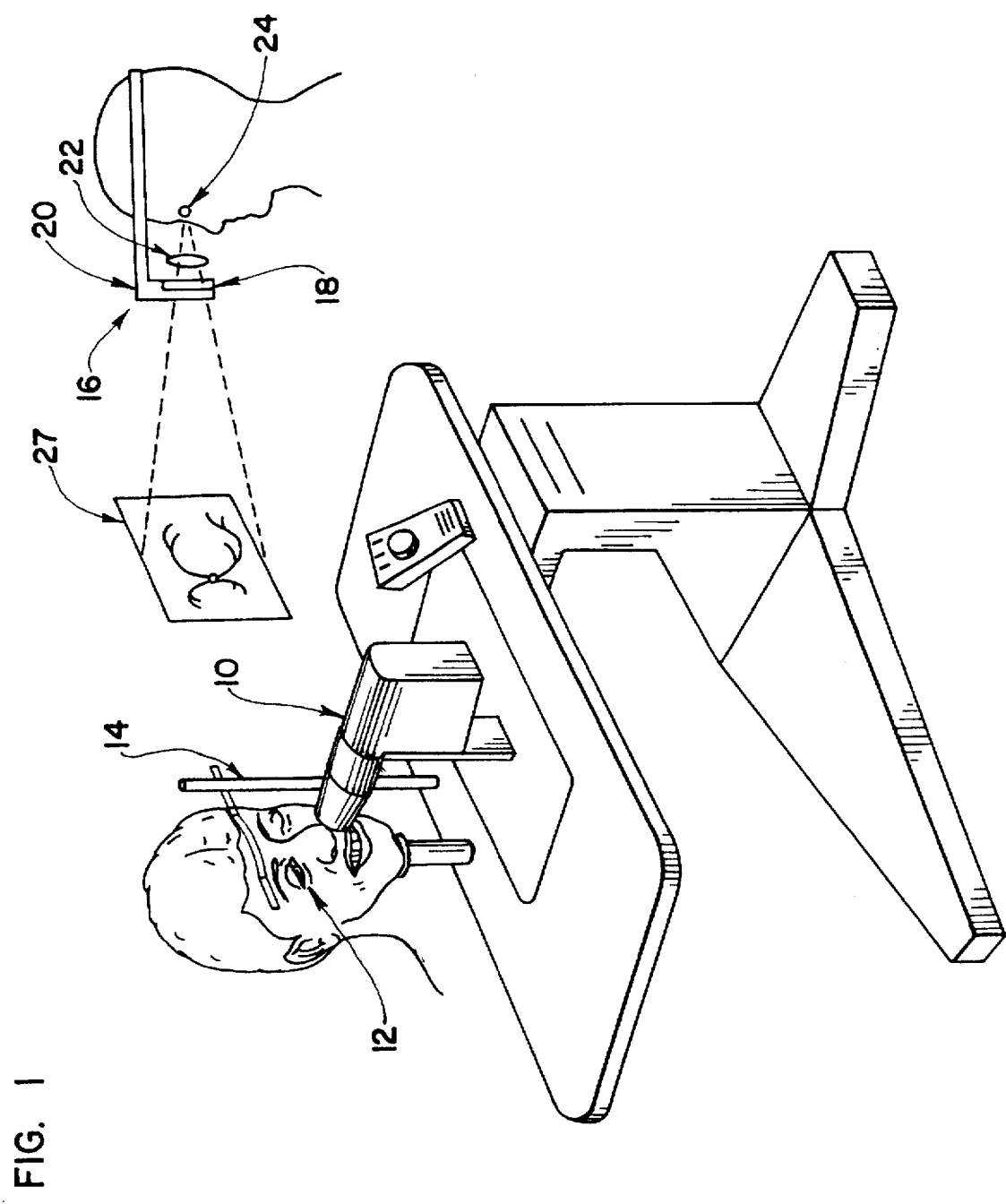
FIG. 1 is a perspective view of a scanning laser ophthalmoscope in accordance with the present invention positioned with respect to a patient and illustrating the image of an interior portion of the patient's eye viewed by an attending clinician through a head mounted display system.

A scanning laser ophthalmoscope 10 in accordance with the present invention as shown in FIG. 1 is positioned with respect to an eye 12 of a patient to be examined so that a clinician can view an interior portion of the patient's eye 12 during an eye examination. The patient preferably rests his head against a headrest 14 that maintains the patient's head in a stable, fixed position during the examination. The patient looks into the ophthalmoscope 10 so that he perceives a fixation target image generated by the ophthalmoscope 10. As the patient fixes his eye on the target image, which may be stationary or moving, the ophthalmoscope 10 simultaneously illuminates a two dimensional area of the interior of the patient's eye. Light reflected by the patient's eye due to this illumination is reflected back to the ophthalmoscope which captures the light and detects an image of an interior portion of the patient's eye as focused thereon. The detected image from the scanning laser ophthalmoscope 10 is coupled to a display so that it can be viewed by a clinician.

The display coupled to the scanning laser ophthalmoscope 10 may be any conventional display. As shown in FIG. 1, the display 18 forms a part of a head mounted display system 16. Specifically, the output of the scanning laser ophthalmoscope 10 controls a liquid crystal display (LCD) 18 to display the captured image of an interior portion of the patient's eye 12. The LCD 18 is mounted on a frame 20 that is worn by the clinician. Also mounted on the frame 20 is a lens 22 that is disposed between the clinician's eye 24 and the LCD 18. The lens 22 is positioned at approximately one focal length (1F) from the LCD 18 so as to project a magnified virtual image 27 of the patient's interior of the eye. The lens 22 preferably has a short focal length, for example, on the order of 16 mm. The clinician views the virtual image 27 of the interior of the patient's eye 12 through one of the clinician's eyes while simultaneously viewing the exterior of the patient's eye 12 via the clinician's other eye which is not blocked by the monocular head mounted display system 16. The clinician can thus position the virtual image 27 so that it is coincident with the clinician's view of the exterior of the patient's eye 12. In this manner, as the patient's visual function is tested via the scanning laser ophthalmoscope 10, the clinician may observe the interior of the patient's eye while simultaneously observing the patient's external eye movements as it tracks the fixation target image generated by the ophthalmoscope 10.

The scanning laser ophthalmoscope 10 as shown in detail in FIGS. 2–7 includes an illumination system 30 for scanning a two dimensional area of illumination that illuminates the interior of the patient's eye 12 with light of various wavelengths applied simultaneously thereto. Different parts of the eye at different depths therein are responsive to the different wavelengths of light to reflect a respective wavelength of light for detection. An eye image capturing and detection system 32 includes a field lens 34 that is moveable so that light reflected at various depths in the eye can be captured and detected. As the field lens 34 is moved, the image of the interior of the patient's eye depicted on the LCD 18, that is coupled to the system 32, automatically changes to an image of the eye's interior at different depths therein. The LCD 18 is preferably a color display so that the image of the eye at a particular depth as displayed on the LCD 18 is presented in the same color as associated with the wavelength of light to which the imaged portion of the eye responds by reflecting the light. Thus, the displayed image includes information that the clinician is familiar seeing under normal white light viewing conditions in addition to the detailed image information provided by the scanning laser ophthalmoscope 10. There are no beating or blanking problems with the image displayed on the LCD 18 due to the orientation of the scanned illumination light from the illumination system 30 with respect to the raster lines of a charge coupled device 36 that detects the light reflected from the patient's eye as discussed in detail below.

The scanning laser ophthalmoscope 10 further includes a video target generating system 38 with a liquid crystal display (LCD) 37 or the like for generating the fixation target for the patient to view during an eye examination as discussed above. The target generating system 38 is separate from the illumination system 30 so as to greatly simplify the electronics of the system. In particular, the target video does not have to be generated in synchronism with the scanning of the illumination as in prior scanning laser ophthalmoscope that generated target images. Further, the illumination system 30 is separate from the eye image capturing and detection system 32 so that in the scanning laser ophthalmoscope 10 of the present invention there is no scanner, mirror or other optical element that totally blocks light reflected from the patient's eye in a given region of the optical path to the capturing and detection system 32. This feature eliminates the shading off problems of prior scanning laser ophthalmoscopes.

Figure 8A:
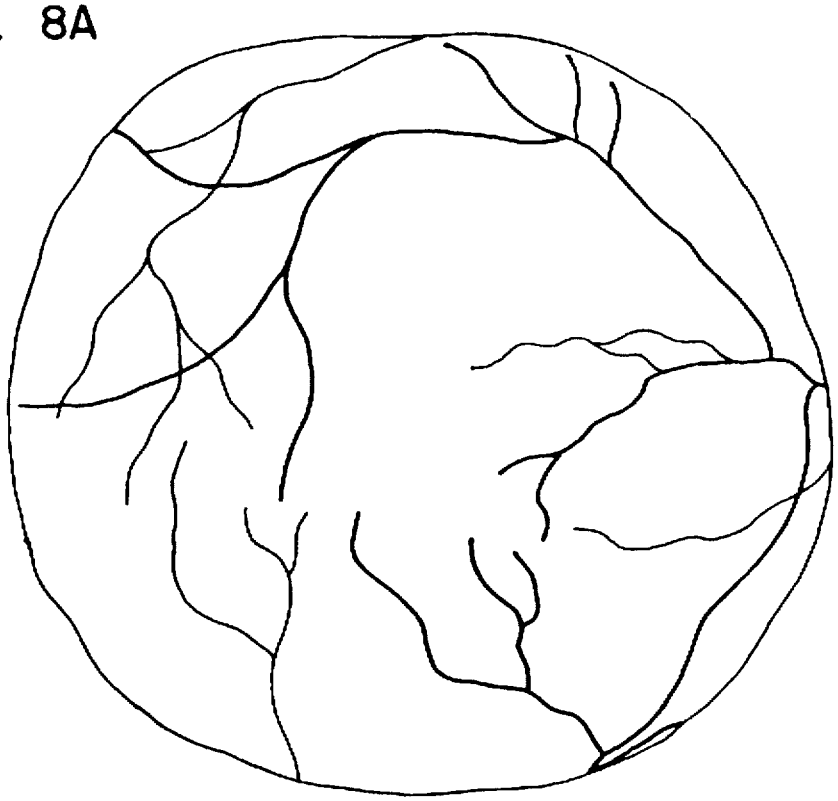
FIGS. 8A and 8B respectively illustrate an image of an eye displayed by the scanning laser ophthalmoscope of FIG. 2 and of an eye image displayed with a prior device that produces a shading off effect.

In order to accomplish the separation of the illumination system 30, eye image capturing and detection system 32 and the video target generating system 38, the scanning laser ophthalmoscope includes a pair of beam splitters 40 and 42. The beam splitter 40 is a partially reflecting illumination mirror that reflects at least 25% of the illumination light from the illumination system 30 to the patient's eye 12 while passing therethrough light reflected from the patient's eye 12 as well as light generated by the LCD 37. The light reflected from the patient's eye 12 and passed through the beam splitter 40 is reflected by the beam splitter 42 to the eye image capturing and detection system 32. The beam splitter 42 may be formed as a partial reflector for reflecting a large percentage of the light impinging from the patient's eye to the eye image capturing and detection system 32 and for passing therethrough only a small percentage of light from the LCD 37. The beam splitter 42 may also be formed as a dichroic mirror passing only a small percentage of the visible spectrum from the liquid crystal display 8 and for reflecting a large percentage of the light reflected from the patient's eye 12 to the eye image capturing and detection system 34. It has been found that the shading off effects plaguing prior scanning laser ophthalmoscopes were caused by an optical element such as a scanner or mirror placed in the optical path from the patient's eye to the detection system. These optical elements block the chief ray from any given image position on its route from the patient's eye to the image detection optics thereby causing shading off. The present invention eliminates this problem by separating the image capturing and detection system 32 from the illumination system 30 and by employing optical elements within the optical path to the eye image capturing and detection system 32 that do not block the chief rays from any given image position on their route to the capturing and detection system 32. As a result, the displayed image of the eye is as shown in FIG. 8A as opposed to an image of the eye as shown in FIG. 8B that has the shading off effect.

Figure 8B:
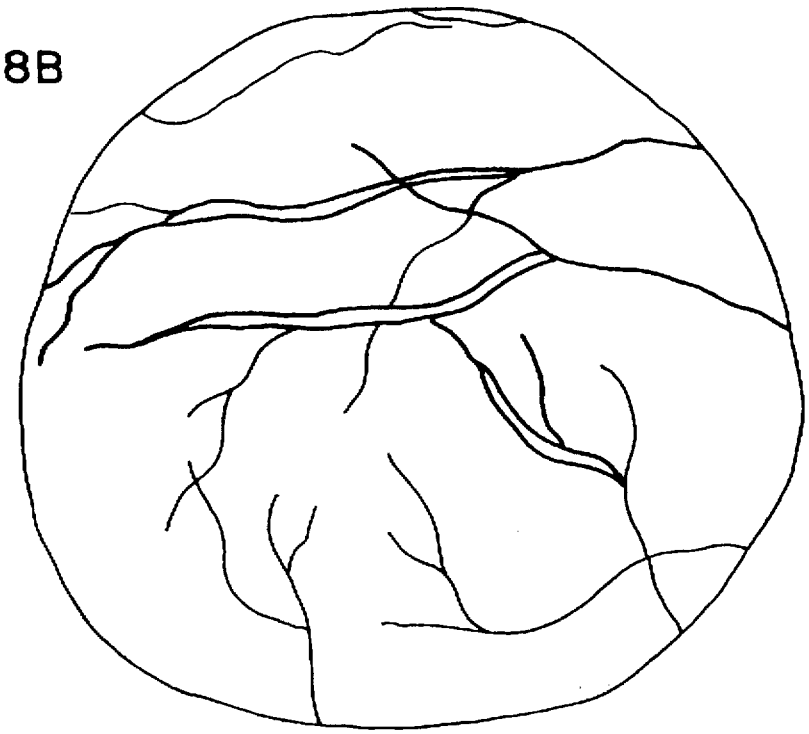

The shading off effect can be seen in FIG. 8B as a darkening of the edges of a feature of the image and as a lightening of the center of the feature. For example, in FIG. 8B the imaged features of blood vessels are shown as dark parallel lines with a gradual lightening towards the center of the blood vessel. This effect is not present in the image displayed by the scanning laser ophthalmoscope 10 of the present invention as depicted in FIG. 8A because the chief ray from any given image position in the eye is not blocked on its route to the image detector of the system 32.

Figure 2:
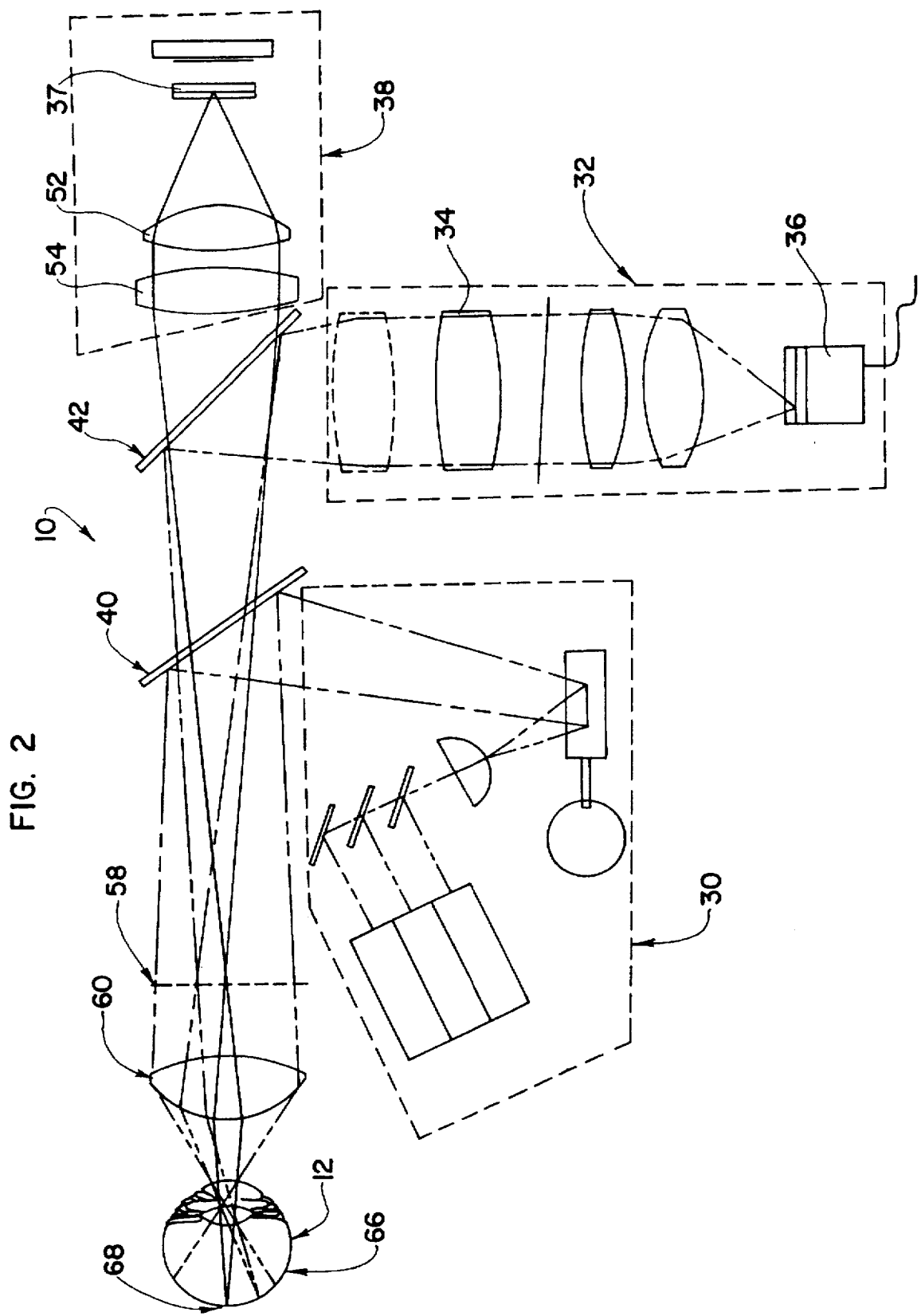
FIG. 2 is a plan view of the scanning laser ophthalmoscope of FIG. 1 shown in relation to the patient's eye.
Figure 3:
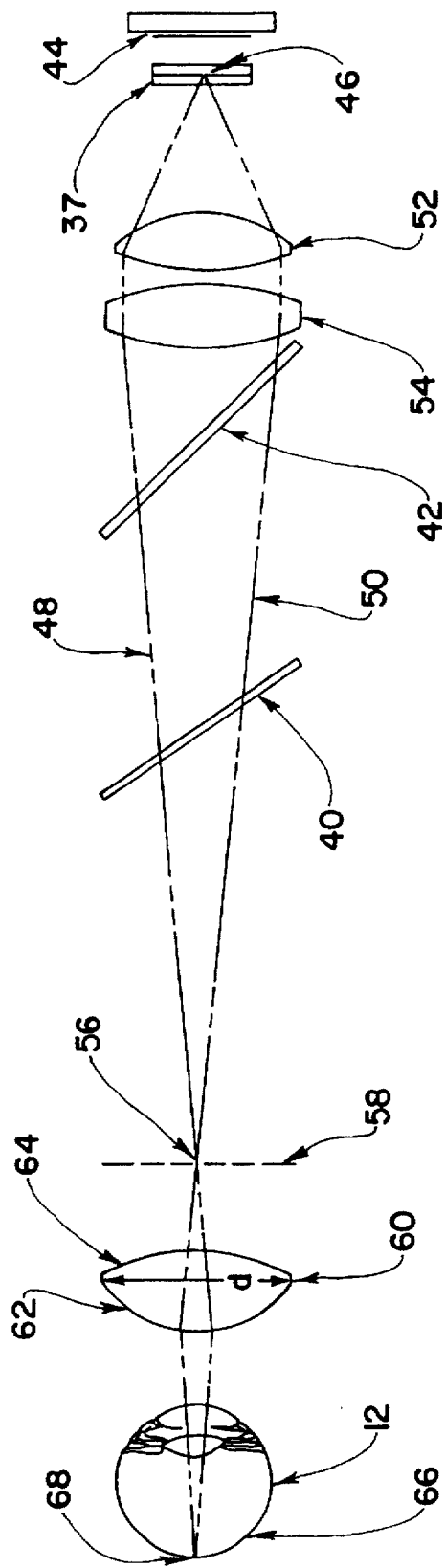
FIG. 3 is a plan view of the target video generation portion of the scanning laser ophthalmoscope of FIG. 2.

As described above, the video target generating system 38 as shown in FIGS. 2 and 3 includes the LCD 37 that is backlit by a light source 44. Any given pixel 46 on the LCD 37 is projected as shown by rays 48 and 50 through a display lens 52. The rays 48 and 50 are focused by a field lens 54 through the beam splitters 42 and 40 to a point 56 on a real image plane 58. The rays from the pixel 46 of the LCD 37 continue their path towards the patient's eye 12 through a nonsymmetric aspheric lens 60. The aspheric lens includes a strong surface 62 and a weaker surface 64 wherein the lens 60 is positioned so that the stronger surface 62 is adjacent the patient's eye 12. The rays from the LCD pixel 46 impinging on the weaker surface 64 of the aspheric lens 60 are partially focused by the weaker surface 64 and are further focused by the stronger or steeper surface 62 of the aspheric objective lens 60 towards the patient's eye 12. The optics of the patient's eye provide the final focus of the rays 48 and 50 of the display pixel 46 onto the fundus 66 of the eye at a point 68 so that it is seen by the patient.

Figure 4:
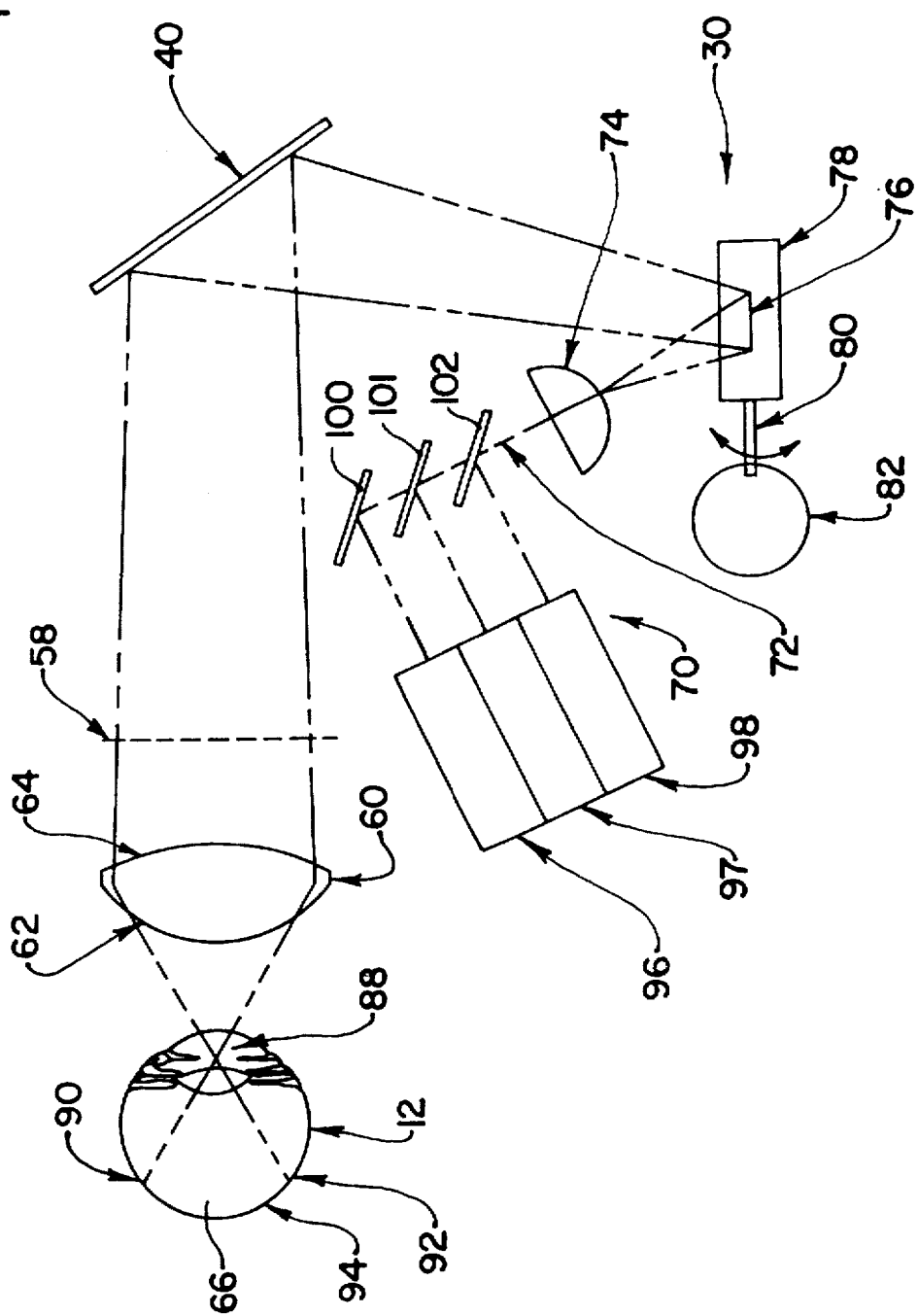
FIG. 4 is a plan view of the illumination portion of the scanning laser ophthalmoscope of FIG. 2.
Figure 5:
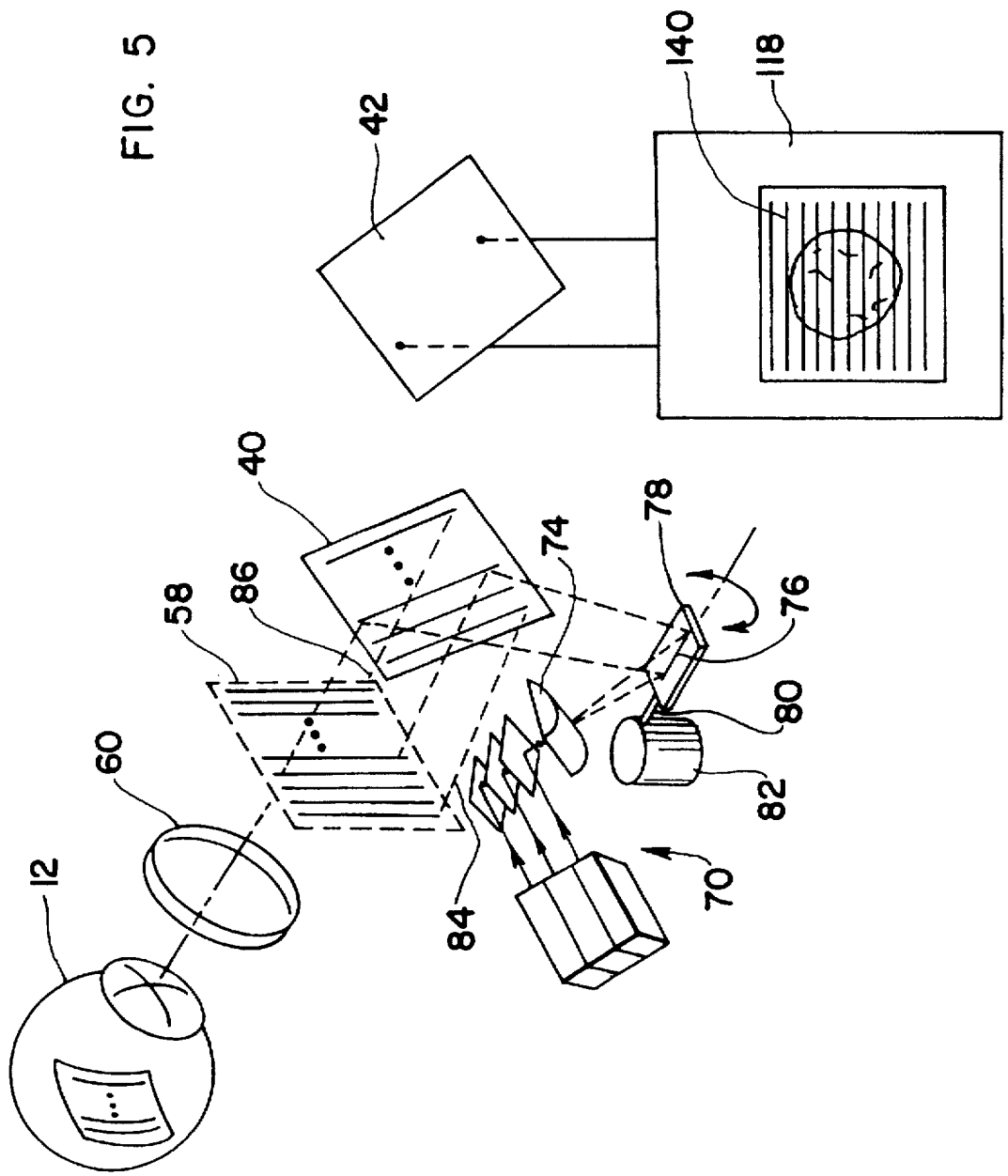
FIG. 5 is a perspective view of the illumination system shown in FIG. 4 and a portion of the eye image capturing and detection portion of the scanning laser ophthalmoscope of FIG. 2.

The illumination system 30 of the scanning laser ophthalmoscope 10 is shown in detail in FIGS. 2, 4 and 5. As shown therein, a laser source 70 generates a laser beam 72 that impinges on a passive, stationary optical element 74 at a point. The passive, stationary optical element 74, which may be a cylindrical lens as shown, generates a line 76 of light from the point of light impinging on the lens 74. The line 76 of laser light is scanned in a direction perpendicular to the direction of the line 76 by a scanner mirror 78 on which the line of light impinges, the scanner mirror 78 being driven by a scanner motor 82 that is coupled to the mirror 78 via a shaft 80. As the scanner mirror 78 vibrates, it scans the line 76 horizontally across the face of the partially reflective beam splitter 40 as shown in FIG. 5 so that a rectangular shaped area of illumination is generated on the face of the beam splitter 40. The beam splitter 40 reflects the rectangular area of illumination light towards the eye 12 so that it is centered on the real image plane 58 and aspheric lens 60. The illumination light as it travels towards the eye 12 is slightly diverging as depicted by the rays 84 and 86. The weaker surface 64 of the aspheric lens makes the slightly diverging illumination light parallel and directs the illumination light to the stronger surface 62 of the aspheric lens 60. The stronger surface 62 of the aspheric lens focuses the illumination light to a point 88 that is centered on the patient's pupil or generally proximate thereto. The illumination light continues its path until it strikes the retina 94 of the eye 12, thus illuminating an area of the patient's eye within the boundaries of the rays 90 and 92. The use of the passive optical element 74 that converts a point of light impinging thereon into a line of light without an external drive signal applied thereto as required by acousto optic modulators and without movement of an element as in scanning mirrors, substantially simplifies the optical system of the present invention and reduces the size thereof. Further, this optical arrangement allows a color image of the interior of the patient's eye at varying depths within the eye to be obtained very easily.

In particular, in order to generate a color image of the interior of the patient's eye 12 at varying depths therein, the laser source 70 includes a number of lasers 96–98 each of which produces a laser beam of a different wavelength, preferably associated with blue, green and red laser light. The laser light of different wavelengths generated by the lasers 96–98 are combined to form a single laser beam 72 by a number of dichroic mirrors 100–102. In the embodiment depicted in FIGS. 2 and 4, each of the dichroic mirrors 100–102 is coated in a way such that the mirror reflects only the wavelength of light associated with its respective laser source. In particular, the dichroic mirror 100 reflects light having a wavelength of the laser source 96. This reflected light passes through the dichroic mirror 101 where it is combined with coaxial light reflected by the mirror 101 from the laser source 97 thus combining light of the two wavelengths associated with the lasers 96 and 97. This combined beam passes through the dichroic mirror 102 where it is combined with light having the selected wavelength of the laser 98 that is reflected coaxially therewith so as to form the single laser beam 72 comprised of the three lasers of different wavelengths from the sources 96–98. As the laser beam 72 is scanned onto the patient's eye 12, as is well known, different parts of the eye at different depths therein respond to different wavelengths of laser light by reflecting laser light of a particular wavelength.

Figure 6:
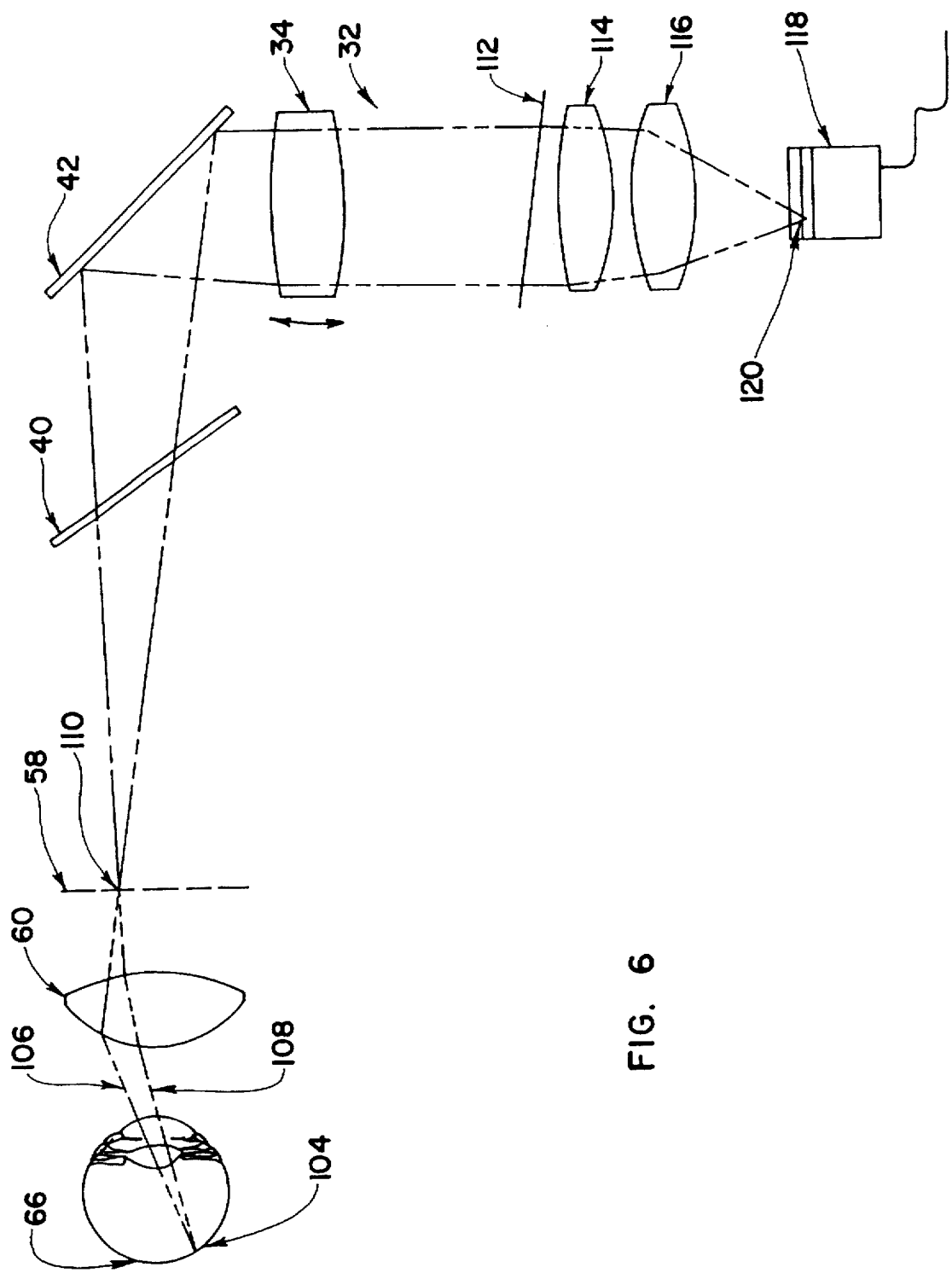
FIG. 6 is a plan view of the eye image capturing and detection system of the scanning laser ophthalmoscope of FIG. 2.

In order to capture and detect a color image of the interior of the patient's eye 12 at varying depths therein, the eye image capturing and detection system 32 includes the moveable field lens 34. More particularly, as shown in FIGS. 2 and 6, an illuminated point 104 on the fundus 66 of the patient's eye 12 reflects light shown by rays 106 and 108 wherein the reflected light is captured and focused by the aspheric lens 60 to a point 110 on the image plane 58. The light reflected from the patient's eye passes through the beam splitter 40 to the beam splitter 42 that reflects the light from the patient's eye 12 to the moveable field lens 34 of the eye image capturing and detection system 32. The light reflected from the patient's eye passes through the field lens 34 and from there through a polarizer film 112 into focusing optics comprised of a pair of lenses 114 and 116 of a charge coupled device (CCD) camera 118. The lenses 114 and 116 focus the rays reflected from the patient's eye onto the image plane of the CCD camera 118 at a point 120.

Figure 7:
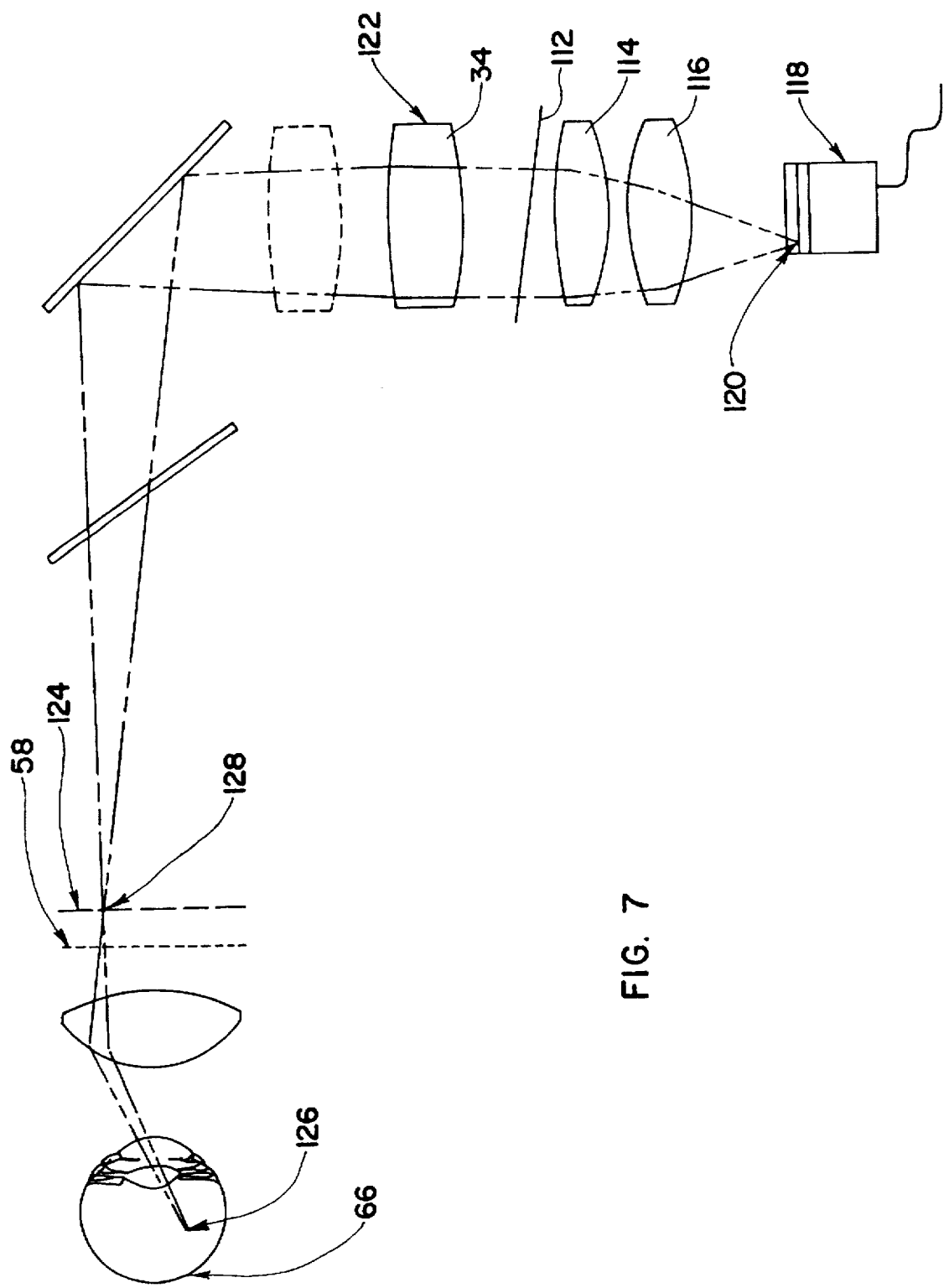
FIG. 7 is an illustration of the eye image capturing and detection system of FIG. 6 with the field lens thereof moved to a different location.

By changing the position of the field lens 34 from that shown in FIG. 6 to the position shown at 122 in FIG. 7 so that it is moved farther from the patient's eye, the real image plane 58 shifts to the position 124 that is closer to the eye image capturing and detection system 32. With this shift in the image plane, the focus of the scanning laser ophthalmoscope 10 is no longer at the fundus 66 of the patient's eye but is brought to a position 126 within the interior of the eye. This point 126 in the interior of the patient's eye that is brought into focus by moving the field lens to the position 122 corresponds to a point 128 on the shifted image plane at the position 124. This point 128 is in turn focused on the CCD camera 118 at the point 120. Thus, by merely moving the field lens 34 of the eye image capturing and detection system 32 to a different position, various images of the interior of the patient's eye 12 at varying depths therein can be obtained. Further, by coupling the CCD camera to a color display 18, as the field lens 34 is moved to bring into focus an image at varying depths within the interior of the patient's eye, the image displayed on the color LCD 18 automatically changes to display the changed image in the color of the associated wavelength of laser light that is reflected by the portion of the eye at that particular depth.

In order to pass only desired light to the detection circuitry of the CCD camera 118, the laser light from the source 70 and in particular from the sources 96–98 is polarized in a first direction and the polarizer film 112 of the eye image capturing and detection system 32 is polarized in a second direction that is different from the first direction. In particular, the polarizer film 112 is preferably polarized in a direction perpendicular to the polarization of the laser light from the source 70. This polarization of the polarizer film 112 blocks unwanted reflections from the patient's cornea, the aspheric lens 60, and other elements of the system from reaching the image plane of the CCD camera 118 so that only the randomized reflected image from the interior of the patient's eye passes through the optical system into the CCD camera.

In addition, it is found that by orienting the scanning of the laser lines onto the patient's eye in a particular manner with respect to the orientation of a raster line of the CCD scanner, beating and blanking problems in the video image depicted on the display 18 from the CCD camera are eliminated. More particularly, as shown in FIG. 5, the raster lines such as the line 140 extends horizontally across the CCD camera 118. The laser line 76 when reflected by the beam splitter 40 onto the eye extends in the vertical direction and is scanned horizontally. When the line of light is thus scanned on the patient's eye 12 it extends vertically i.e. perpendicular to the direction of the horizontal raster line 140 as referenced to the patient's eye. Because the line of light scanned onto the patient's eye 12 extends perpendicular to the direction of the raster line 140, beating and blanking problems in the displayed video image are eliminated.

As is apparent from the above description, the aspheric lens 60 of the present invention focuses the target image from the LCD 37 onto the patient's eye 12; the aspheric lens 60 focuses the illumination light from the illumination system 30 on an area of the patient's eye that is generally proximate to the pupil; and the aspheric lens 60 intercepts light reflected from the patient's eye 12 and focuses the intercepted light onto an image plane 58 that is disposed between the aspheric lens and the eye image capturing and detection system 32. In order to provide such an aspheric lens, each surface 62 and 64 of the lens is preferably described by the polynomial function:

$$f(Y, A_2, A_4, A_6, C, cc) = A_2 Y^2 + A_4 Y^4 + A_6 Y^6 + CY^2/(1 + \sqrt{1 - C^2 cc})$$

where $A_2$, $A_4$ and $A_6$ are constants; C represents the curvature of the surface; and cc represents the conic constant. For the stronger surface 62 of the lens 60, these values should be within the following ranges:

$0.0 < A_2 < 0.003$ $-0.02 < A_4 < 0.02$ $-0.01 < A_6 < 0.01$ $-0.1 < C < 0.0$ $-2.0 < cc < 1.0$

For the weaker surface 64 of the lens 60 these values should be within the following ranges:

$-0.003 < A_2 < 0.0$ $0.0 < A_4 < 0.001$ $-0.001\ A_6 < 0.001$ $0.03 < C < 0.06$ $-2.0 < cc < 0.0$

Further the curvature C of the weaker surface 64 is preferably greater than $-\frac{1}{2}$ times the curvature C of the stronger surface 62.

In a preferred embodiment of the present invention, the stronger surface 62 of the lens 60 has the values of: $A_2 = 0.000444$, $A_4 = 0.000001$, $A_6 = 0.0$, $C = -0.092$ and $cc = -0.933$; whereas the weaker surface 64 of the lens 60 has values of: $A_2 = -0.00243$, $A_4 = 0.0000012$, $A_6 = 0.01$ $C = 0.045$ and $cc = -1.213$.

While the diameter d of the lens 60 may be varied, the preferred diameter is 35 millimeters. The aspheric lens 60 produces a 60° field of view for the scanning laser ophthalmoscope 10 which is extremely wide compared to prior scanning laser ophthalmoscopes. Further, the real image produced by the aspheric lens 60 is substantially free from distortions.

Many modifications and variations of the present invention are possible in light of the above teachings. Thus, it is to be understood that, within the scope of the appended claims, the invention may be practiced otherwise than as described hereinabove.

What is claimed and desired to be secured by letters patent is:

1. A scanning laser ophthalmoscope comprising:

a source of laser light;

a scanning system for generating a two dimensional area of illumination from said laser light;

a first beam splitter for reflecting said illumination from said scanning system towards a patient's eye and for passing therethrough light reflected from said patient's eye;

an image capturing system for detecting light reflected from said patient's eye and for generating an image of an interior portion of said eye from the detected light;

a second beam splitter coaxial with said first beam splitter for receiving light reflected from said patient's eye and passed through said first beam splitter and for reflecting said light to said image capturing system; and a video display for generating a target image, said video display being positioned with respect to said first and second beam splitters such that light from said video display passes through said first and second beam splitter to said patient's eye so that said target image is perceivable by the patient.

2. A scanning laser ophthalmoscope as recited in claim 1 including a nonsymmetric aspheric lens disposed between said patient's eye and said first beam splitter for focusing said target image from said display onto the patient's eye, said aspheric lens focusing said illumination light from said first beam splitter on an area generally proximate to the patient's pupil and said aspheric lens intercepting light reflected from said patient's eye and focusing said intercepted light onto an image plane disposed between said aspheric lens and said first beam splitter.

3. A scanning laser ophthalmoscope as recited in claim 1 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

4. A scanning laser ophthalmoscope as recited in claim 3 wherein said passive optical element is a cylindrical lens.

5. A scanning laser ophthalmoscope as recited in claim 1 wherein said video display is coaxial with said first and second beam splitters.

6. A scanning laser ophthalmoscope as recited in claim 1 wherein said video display is a liquid crystal display that generates a moving target image.

7. A scanning laser ophthalmoscope as recited in claim 1 wherein said source of laser light generates laser light having a plurality of wavelengths that are simultaneously scanned by said scanning system and reflected towards the patient's eye by said first beam splitter and said image capturing system includes a moveable field lens to automatically capture and generate an image of different parts of the eye at various depths therein in response to movement of said field lens.

8. A scanning laser ophthalmoscope as recited in claim 7 wherein said source of laser light includes a plurality of lasers operating at different frequencies for generating a plurality of lasers with different wavelengths, said lasers being combined by one or more partially reflecting mirrors into one beam of laser light directed to said scanning system.

9. A scanning laser ophthalmoscope as recited in claim 1 wherein said image capturing system includes an image detector responsive to light impinging thereon for generating signals representative thereof; and a head mounted display system having a video display to which said signals from said image detector are coupled for displaying an image of the interior portion of the patient's eye; and an optical system that projects a magnified image of said displayed image of the interior portion of the patient's eye at a distance from the user so that it can appear substantially coincident with the patient's eye when a user of the head mounted display system directs his sight towards the patient's eye.

10. A scanning laser ophthalmoscope as recited in claim 9 wherein said optical system of said head mounted display system includes a lens positioned between an eye of said user and said video display at a distance from said video display approximately equal to one focal length of the lens.

11. A scanning laser ophthalmoscope as recited in claim 10 wherein the focal length of said lens is within the approximate range of 12 mm to 3 mm.

12. A scanning laser ophthalmoscope as recited in claim 1 wherein said laser light from said source is polarized in a first direction and said image capturing system includes an image detector that is responsive to light impinging thereon for generating signals representative thereof; and a polarizer disposed between said image detector and said second beam splitter, said polarizer being polarized in a second direction different from said first direction of polarization of said laser light to pass desired light to said image detector.

13. A scanning laser ophthalmoscope as recited in claim 12 wherein said polarizer is polarized perpendicular to the polarization of said laser light.

14. A scanning laser ophthalmoscope as recited in claim 1 wherein said image capturing system includes an image detector having a plurality of raster lines extending in a first direction to provide a representation of an image of an interior portion of the user's eye and said scanning system generates a line of light that is scanned in a direction perpendicular to said line and directed to the patient's eye by said first beam splitter so that said line of light when scanned on said eye extends perpendicular to said first direction of the raster line relative to said eye's image.

15. An illumination system for a scanning laser ophthalmoscope comprising:

a source of laser light;

a passive, stationary optical element positioned in a path of said laser light such that said light impinges on said passive optical element at a point, said optical element generating a line of light from said point of light impinging thereon;

a scanner for scanning said line of light in a direction perpendicular to the direction in which said line extends to generate a two dimensional area of illumination; and an optical system for directing said two dimensional area of illumination onto the fundus of the eye.

16. An illumination system for a scanning laser ophthalmoscope as recited in claim 15 wherein said passive optical element is a cylindrical lens.

17. An illumination system for a scanning laser ophthalmoscope as recited in claim 15 wherein said optical system includes a nonsymmetric aspheric lens for focusing said light on an area generally proximate to the patient's pupil.

18. An illumination system for a scanning laser ophthalmoscope as recited in claim 15 wherein said optical system includes a beam splitter for reflecting light from said scanner towards the patient's eye and for allowing light reflected from said patient's eye to pass through said beam splitter to prevent a chief ray from said patient's eye from being blocked.

19. A scanning laser ophthalmoscope comprising:

a source of laser light polarized in a first direction;

a scanning system for generating a two dimensional area of illumination from said laser light;

a first beam splitter for directing said illumination towards a patient's eye and for passing therethrough light reflected from said patient's eye;

a nonsymmetric aspheric lens for focusing illumination light received from said beam splitter on an area generally proximate to the patient's pupil and for focusing light reflected from said patient's eye onto an image plane disposed between said aspheric lens and said first beam splitter; and a polarizer disposed in a path of said light reflected from said patient's eye and passed through said first beam splitter, said polarizer being polarized in a second direction different from said first direction of the polarization of said laser light to pass desired reflected light for detection.

20. A scanning laser ophthalmoscope as recited in claim 19 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

21. A scanning laser ophthalmoscope as recited in claim 20 wherein said passive optical element is a cylindrical lens.

22. A scanning laser ophthalmoscope as recited in claim 19 wherein said polarizer is polarized perpendicular to the polarization of said laser light.

23. In a scanning laser ophthalmoscope, a system for illuminating an interior portion of the user's eye and for projecting a movable target on the eye comprising:

a source of laser light;

a scanning system for generating a two dimensional area of illumination from said laser light;

a first beam splitter for reflecting said illumination from said scanning system towards a patient's eye and for passing therethrough light reflected from said patient's eye so that an image of an interior portion of the eye can be detected; and a video display for generating a moveable target image; and optics for projecting light from said display through said beam splitter towards the user's eye so that said target image is perceivable by the user without scanning the target image onto the eye.

24. A scanning laser ophthalmoscope as recited in claim 23 including a nonsymmetric aspheric lens disposed between said patient's eye and said first beam splitter for focusing said target image from said display onto the patient's eye so that it is perceivable by the patient and said aspheric lens focusing said illumination light from said beam splitter on an area generally proximate to the patient's pupil.

25. A scanning laser ophthalmoscope as recited in claim 23 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

26. A scanning laser ophthalmoscope as recited in claim 25 wherein said passive optical element is a cylindrical lens.

27. A scanning laser ophthalmoscope as recited in claim 23 wherein said video display is coaxial with said first beam splitter.

28. A scanning laser ophthalmoscope as recited in claim 23 wherein said video display is a liquid crystal display.

29. A scanning laser ophthalmoscope comprising:
  a source of a laser light beam having a plurality of wavelengths of laser light therein;
  a scanning system for generating a two dimensional area of illumination from said laser light beam wherein said plurality of wavelengths of laser light are simultaneously scanned;
  an optical system for directing said two dimensional area of illumination onto the fundus of the eye and for receiving light reflected from said patient's eye; and
  a field lens for receiving from said optical system light reflected from said patient's eye, said field lens being moveable so as to bring into focus different parts of the user's eye at various depths therein.

30. A scanning laser ophthalmoscope as recited in claim 29 wherein said source of laser light includes a plurality of lasers operating at different frequencies for generating a plurality of lasers with different wavelengths, said lasers being combined by one or more dichroic mirrors into one beam of laser light directed to said scanning system.

31. A scanning laser ophthalmoscope as recited in claim 29 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

32. A scanning laser ophthalmoscope as recited in claim 31 wherein said passive optical element is a cylindrical lens.

33. A scanning laser ophthalmoscope as recited in claim 29 wherein said optical system includes a nonsymmetric aspheric lens for focusing said illumination light from said scanning system on an area generally proximate to the patient's pupil and for focusing light reflected from said patient's eye onto an image plane disposed between said aspheric lens and said movable field lens.

34. A scanning laser ophthalmoscope as recited in claim 29 wherein said optical system includes a beam splitter to separate the optical path from the patient's eye to said scanning system and to said field lens.

35. A scanning laser ophthalmoscope as recited in claim 34 wherein said optical system includes a nonsymmetric aspheric lens disposed between said beam splitter and a patient's eye.

36. A scanning laser ophthalmoscope as recited in claim 29 including an image detector for receiving from said field lens light of said plurality of wavelengths reflected from said patient's eye and responsive to said wavelengths of laser light for generating color eye image signals; and a color video display for displaying a video image of the interior of the user's eye at various depths therein in different colors so that as said field lens is moved said video image automatically changes to depict said various portions of the user's eye in said different colors.

37. A scanning laser ophthalmoscope as recited in claim 36 wherein said color video display is mounted on a frame to be worn on a user's head as a portion of a head mounted display system and including an optical system mounted on said frame for projecting a magnified image of said color video image of the interior of the patient's eye at a distance from the user so that it can appear substantially coincident with the patient's eye when the user directs his view towards the patient's eye.

38. A scanning laser ophthalmoscope as recited in claim 37 wherein said optical system of said head mounted display system includes a lens positioned between an eye of said user and said video display at a distance from said video display approximately equal to one focal length of the lens.

39. A scanning laser ophthalmoscope as recited in claim 38 wherein the focal length of said lens is within the approximate range of 12 mm to 33 mm.

40. A scanning laser ophthalmoscope as recited in claim 29 wherein said laser light of said laser light beam is polarized in a first direction and including a polarizer for receiving from said field lens light reflected from said patient's eye, said polarizer being polarized in a second direction different from said first direction of the polarization of said laser light to pass desired reflected light for detection.

41. A scanning laser ophthalmoscope as recited in claim 40 wherein said polarizer is polarized perpendicular to the polarization of said laser light.

42. A scanning laser ophthalmoscope comprising:
  a source of a laser light beam having a plurality of wavelengths of laser light therein;
  a scanning system for generating a two dimensional area of illumination from said laser light beam directed to a patient's eye to illuminate the fundus;
  an image capturing and detection system for detecting light reflected from the patient's eye and for generating an image of an interior portion of the eye from the detected light;
  a beam splitter disposed in the optical paths between said scanning system and the patient's eye and between the image capturing system and the patient's eye for separating the scanning system that illuminates the eye for detection of an image of the interior thereof from the image capturing and detection system whose operation depends on the illumination without blocking a chief ray from a point in the patient's eye from reaching said image capturing and detection system.

43. A scanning laser ophthalmoscope as recited in claim 42 including a target image video generating system for generating a target image projected onto the patient's eye and an additional beam splitter disposed in the optical paths between the image capturing and detection system and the target image video generating system.

44. A scanning laser ophthalmoscope as recited in claim 42 wherein said beam splitters are coaxial.

45. A scanning laser ophthalmoscope as recited in claim 42 wherein said source of laser light generates laser light having a plurality of wavelengths that are simultaneously scanned by said scanning system and directed to the patient's eye and said image capturing and detection system includes a moveable field lens to automatically capture and generate an image of different parts of the eye at various depths therein in response to movement of said field lens.

46. A scanning laser ophthalmoscope as recited in claim 45 wherein said source of laser light includes a plurality of lasers operating at different frequencies for generating a plurality of lasers with different wavelengths, said lasers being combined by one or more partially reflecting mirrors into one beam of laser light directed to said scanning system.

47. A scanning laser ophthalmoscope as recited in claim 42 wherein said laser light from said source is polarized in a first direction and said image capturing system includes an image detector that is responsive to light impinging thereon for generating signals representative thereof; and a polarizer disposed between said image detector and said beam splitter, said polarizer being polarized in a second direction different from said first direction of polarization of said laser light to pass desired light to said image detector.

48. A scanning laser ophthalmoscope as recited in claim 47 wherein said polarizer is polarized perpendicular to the polarization of said laser light.

49. A scanning laser ophthalmoscope as recited in claim 42 wherein said image capturing system includes an image detector having a plurality of raster lines extending in a first direction to provide a representation of an image of an interior portion of the user's eye and said scanning system generates a line of light that is scanned in a direction perpendicular to said line and directed to the patient's eye so that said line of light when scanned on said eye extends perpendicular to said first direction of the raster line relative to said eye's image.

50. A scanning laser ophthalmoscope comprising:
   a source of a laser light beam having a plurality of wavelengths of laser light therein;
   a passive, stationary optical element positioned in a path of said laser light such that said light beam impinges on said passive optical element at a point, said optical element generating a line of light from said point of light impinging thereon;
   a scanner for scanning said line of light in a direction perpendicular to the direction in which said line extends to generate a two dimensional area of illumination of light with said plurality of wavelengths; and
   an optical system for directing said two dimensional area of illumination onto the fundus of the eye and for receiving light reflected from said patient's eye; and
   a field lens for receiving from said optical system light reflected from said patient's eye, said field lens being moveable so as to bring into focus different parts of the user's eye at various depths therein.

51. A scanning laser ophthalmoscope as recited in claim 50 including a beam splitter disposed in the optical paths between said scanner and the patient's eye and between said field lens and the patient's eye.

52. A scanning laser ophthalmoscope as recited in claim 51 including a target image video generating system for generating a target image projected onto the patient's eye and an additional beam splitter disposed in the optical paths between the image capturing and detection system and the target image video generating system.

53. A scanning laser ophthalmoscope as recited in claim 52 wherein said laser light from said source is polarized in a first direction and said image capturing system includes an image detector that is responsive to light impinging thereon for generating signals representative thereof; and a polarizer disposed in the optical path to said image detector said polarizer being polarized in a second direction different from said first direction of polarization of said laser light to pass desired light to said image detector.

54. A scanning laser ophthalmoscope comprising:
   a source of laser light;
   a scanning system for generating a line of light and scanning said line in a direction perpendicular to said line;
   an optical system for directing said scanned light to the patient's eye so that said line of light when scanned on said eye extends in a first direction;
   an image capturing system with an image detector having a plurality of raster lines extending in a first direction to provide a representation of an image of an interior portion of the user's eye, said raster lines extending in a second direction relative to said eye image that is perpendicular to said first direction of said scanned line of light.

55. A scanning laser ophthalmoscope comprising:
   a source of laser light;
   a scanning system for generating a two dimensional area of illumination from said laser light;
   an image capturing system for detecting light reflected from said patient's eye and for generating an image of an interior portion of said eye from the detected light;
   a target image video display for generating a target image directed to the patient's eye; and
   a nonsymmetric aspheric lens for focusing said target image from said display onto the patient's eye, said aspheric lens focusing said illumination light from said scanning system on an area generally proximate to the patient's pupil and said aspheric lens intercepting light reflected from said patient's eye and focusing said intercepted light onto an image plane disposed between said aspheric lens and said image capturing system.

56. A scanning laser ophthalmoscope as recited in claim 55 wherein said scanning system includes a scanner with a movable reflective surface and a passive, stationary optical element positioned in a path of said laser light such that said light impinges on said passive optical element at a point, said optical element generating a line of light from said point of light impinging thereon and said scanner scans said line of light in a direction perpendicular to the direction in which said line extends to generate a two dimensional area of illumination.

57. A scanning laser ophthalmoscope as recited in claim 56 wherein said passive optical element is a cylindrical lens.

58. A scanning laser ophthalmoscope as recited in claim 55 wherein said source of laser light generates laser light having a plurality of wavelengths that are simultaneously scanned by said scanning system and said image capturing system includes a moveable field lens to automatically capture and generate an image of different parts of the eye at various depths therein in response to movement of said field lens.

59. A scanning laser ophthalmoscope as recited in claim 58 wherein said source of laser light includes a plurality of lasers operating at different frequencies for generating a plurality of lasers with different wavelengths, said lasers being combined by one or more partially reflecting mirrors into one beam of laser light directed to said scanning system.

60. A scanning laser ophthalmoscope as recited in claim 55 wherein said image capturing system includes an image detector responsive to light impinging thereon for generating signals representative thereof; and a head mounted display system having a video display to which said signals from said image detector are coupled for displaying an image of the interior portion of the patient's eye; and an optical system that projects a magnified image of said displayed image of the interior portion of the patient's eye at a distance from the user so that it can appear substantially coincident with the patient's eye when a user of the head mounted display system directs his sight towards the patient's eye.

61. A scanning laser ophthalmoscope as recited in claim 55 wherein said image capturing system includes an image detector having a plurality of raster lines extending in a first direction to provide a representation of an image of an interior portion of the user's eye and said scanning system generates a line of light that is scanned in a direction perpendicular to said line and directed to the patient's eye so that said line of light when scanned on said eye extends perpendicular to said first direction of the raster line.

* * * * *

Disclaimer 5,784,148 - Gregory Lee Heacock, Atlanta, Ga. WIDE FIELD OF VIEW SCANNING LASER OPHTHALMOSCOPE. Patent dated Jul. 21, 1998. Disclaimer filed Sept. 4, 1998, by the assignee, Odyssey Optical Systems, LLC.

Hereby enters this disclaimer to claims 1-14 and 17-61 of said patent.
*(Official Gazette, May 18, 1999)*